United States Patent [19]
Krumbholz et al.

[11] Patent Number: 6,042,840
[45] Date of Patent: Mar. 28, 2000

[54] COMPONENT OF A SKIN CARE AGENT

[75] Inventors: Rudolf Krumbholz, Holving, France; Peter Lembke, Tarragona, Spain

[73] Assignee: K. D. Pharma GmbH, Bexbach, Germany

[21] Appl. No.: 09/039,535

[22] Filed: Mar. 16, 1998

[30] Foreign Application Priority Data

Mar. 21, 1997 [DE] Germany .......................... 197 11 777

[51] Int. Cl.$^7$ .............................. A61K 6/00; A01N 32/00

[52] U.S. Cl. ........................ 424/401; 514/558; 514/560; 514/844; 514/846; 514/847

[58] Field of Search ........................... 424/401; 514/560, 514/845, 844, 846, 847, 558

[56] References Cited

U.S. PATENT DOCUMENTS 4,792,418  12/1988  Rubin et al. .......................... 260/412
5,194,448   3/1993  Coupland et al. ..................... 514/558

*Primary Examiner*—Thurman K. Page
*Assistant Examiner*—Todd D Ware
*Attorney, Agent, or Firm*—Friedrich Kueffner

[57] ABSTRACT

A urea-containing component of a skin care agent or skin preparation, wherein the urea forms inclusion compounds with fatty acids and/or fatty acid compounds, so that fat is made available for skin care which is protected against oxidation. A method of manufacturing the urea-containing component of a skin care agent includes cooking an oil or a mixture of fatty acid ethyl esters manufactured from an oil with urea in a solvent in a non-oxidizing atmosphere until the urea has been dissolved, permitting the mixture to cool, and finally cooling the mixture to a final temperature of below 10° C. and separating the resulting precipitate.

15 Claims, No Drawings

COMPONENT OF A SKIN CARE AGENT

BACKGROUND OF THE INVENTION

1. Field of the Invention

The present invention relates to a urea-containing component of a skin care agent or skin preparation.

2. Description of the Related Art

Urea is frequently found in creams and salves as a humectant or moistening agent for the skin.

SUMMARY OF THE INVENTION

It is the primary object of the present invention to make it possible to utilize urea for skin care to a greater extent than in the past.

In accordance with the present invention, it is provided for this purpose that the urea forms inclusion compounds with fatty acids and/or fatty acid compounds.

In this manner, fat is made available for skin care which is protected against oxidation.

The various features of novelty which characterize the invention are pointed out with particularity in the claims annexed to and forming a part of the disclosure. For a better understanding of the invention, its operating advantages, specific objects attained by its use, reference should be had to the following descriptive matter in which there are described preferred embodiments of the invention.

DESCRIPTION OF THE PREFERRED EMBODIMENTS

The protection of compounds included into the urea lattice against atmospheric oxygen is known in the art, as described, for example, in "RÖMPP CHEMIE LEXIKON", 9th edition, page 3085, where it is stated that urea may include straight-chain hydrocarbons and weakly branched aliphatic compounds in a channel of its lattice which, in this case, is a hexagonal lattice, wherein n-octane is included, while isooctane is not included. A mixture of alkanes can be fractioned by means of urea. Technically utilized is the formation of inclusion compounds of urea in the separation of hydrocarbon mixtures, in the dewaxing of crude oil and for catalysts, etc. In addition, branched and cyclic aliphatic compounds can be included in the larger lattice of thiourea.

It has now surprisingly been found that urea forms inclusion compounds also with multiple unsaturated fatty acids whose molecules have a substantial curvature. This is at least true in those cases in which no greater portions of fatty acids with straight-chain or essentially straight-chain molecules are present.

Accordingly, in accordance with a particularly advantageous embodiment and further development of the present invention, it is proposed to intercalate into the urea multiple unsaturated fatty acids which are effective in skin care. In particular, omega 3-fatty acids are used for this purpose, wherein the body utilizes these fatty acids for forming membranes. In addition, the omega 3-fatty acids have anti-inflammatory properties. Consequently, they are suitable for medicinal salves.

The present invention provides another significant further development. It has been found that, in the inclusion compound with urea, fatty acids produced from fish oil lose their odor which otherwise cannot be prevented, as is known primarily from fish-liver oil salves. This is particularly significant in the case of omega 3-fatty acids because these fatty acids can practically only be obtained from fish oil.

To be considered particularly in this respect are eicosapenteic acid, docusapenteic acid and docosahexeic acid, which are all omega 3-fatty acids, but also arachidonic acid and octadecatetreic acid which occur partially in omega 3-configuration.

Even if not expressly mentioned herein, fatty acids are always intended to include compounds thereof. These compounds are primarily ethyl esters. The component of a skin care agent according to the present invention is to be understood to be an initial product used for the manufacture of a skin care agent as well as a component present in the finished skin care agent.

Finally, a particularly advantageous aspect of the present invention is the fact that it provides a useful possibility of using filter residues which are obtained by an oil separation by forming inclusion compounds with urea. In the case of suitable oil mixtures, these filter residues only have to be washed, for example, with hexane, dried and ground, preferably to below 50 µm.

In the following, the present invention will be described in more detail with the aid of examples.

Various mixtures of fatty acid ethyl esters were each cooked with urea in ethanol in a nitrogen atmosphere with return flow until the urea was completely dissolved. Subsequently, the mixture was allowed to cool slowly and, after about 6–8 hours, was cooled to a final temperature of between 5° and 10° C. The resulting precipitate was separated by filtering, was washed with hexane and was dried and ground.

In the following, as was the case above, only fatty acids are mentioned but are intended to include their esters.

In each example, 20 g oil (fatty acid mixture) and 40 g urea were added to 400 g 100% ethanol.

EXAMPLE 1

Used as initial oil was a fraction of a fish oil obtained from a chromatographic separation with supercritical carbon dioxide as mobile phase, wherein the fraction contained docosahexeic acid (22:6) and docosapenteic acid (22:5), as well as heneicosapenteic acid (21:5) and a portion of eicosapenteic acid (20:5).

In the following table, the portions of the fatty acids in the initial and in the filter residue are listed:

| Fatty Acid | Initial Oil | Filter Residue |
|---|---|---|
| 20:5 | 18.6 | 12.52 |
| 21:5 | 7.1 | 7.99 |
| 22:5 | 9.3 | 18.68 |
| 22:6 | 59.7 | 57.06 |

EXAMPLE 2

Used as initial oil was a fraction of a fish oil from a chromatographic separation with supercritical carbon dioxide as the mobile phase, wherein the fraction contained the principal portion of the eicosapenteic acid (20:5), arachidonic acid (20:4) omega 3, arachidonic acid (20:4) omega 6 as well as additional fatty acids.

In the following table, the portions of the fatty acids in the initial oil and in the filter residue are listed.

| Fatty Acid | Initial Oil | Filter Residue |
| --- | --- | --- |
| 18:0 | 1.44 | 4.24 |
| 18:1 | 2.07 | 5.37 |
| 18:2 | 0.80 | 2.16 |
| 18:4 | 3.88 | 12.49 |
| 20:4 omega 6 | 2.60 | 2.56 |
| 20:4 omega 3 | 2.84 | 6.08 |
| 20:5 | 80.61 | 54.46 |

EXAMPLE 3

The initial oil consisted of a mixture enriched with eicosapenteic acid (20:5).

In the following table, the portions of fatty acids in the initial oil and in the filter residue are listed:

| Fatty Acid | Initial Oil | Filter Residue |
| --- | --- | --- |
| 18:1 | 11.72 | 41.54 |
| 18:2 | 3.77 | 14.5 |
| 18:4 | 2.12 | 15.8 |
| 20:4 omega 6 | 1.58 | — |
| 20:4 omega 3 | 1.77 | 0.96 |
| 20:5 | 47.52 | 6.12 |
| 21:5 | 1.62 | — |
| 22:5 | 3.52 | — |
| 22:6 | 11.26 | — |

By comparing examples 1 and 2 with example 3, it can be seen that greater quantities of fatty acids with straight-chain molecules or essentially straight-chain molecules, as in 18:1, impair the intercalation of the multiple unsaturated fatty acids, and, therefore, should be reduced previously as much as possible. In general, the above-described method makes it possible to include approximately half of the omega 3-fatty acids of a mixture in the urea.

While specific embodiments of the invention have been described in detail to illustrate the inventive principles, it will be understood that the invention may be embodied otherwise without departing from such principles.

We claim:

1. A urea-containing component of a skin care agent, the component comprising inclusion compounds of the urea with at least one of multiple unsaturated fatty acids and multiple unsaturated fatty acid compounds.

2. The component according to claim 1, wherein the fatty acid compounds are fatty acid ethyl esters.

3. The component according to claim 1, wherein at least a portion of the fatty acids are omega 3-fatty acids.

4. The component according to claim 1, wherein the fatty acids are selected from the group consisting of octadecatetreic acid, arachidonic acid, eicosapenteic acid, docosapenteic acid and docosahexeic acid.

5. The component according to claim 1, wherein the inclusion compounds are comprised of filter residue obtained from an oil separation.

6. The component according to claim 6, wherein the filter residue forms the component essentially chemically unchanged.

7. A method of manufacturing a urea-containing component of a skin care agent, the method comprising cooking an oil or a mixture of fatty acid ethyl esters manufactured from an oil with urea in a solvent in a non-oxidizing atmosphere until the urea has been dissolved, permitting the mixture to cool, and finally cooling the mixture to a final temperature of below 10° C. and separating the resulting precipitate.

8. The method according to claim 7, wherein the solvent is ethanol.

9. The method according to claim 7, wherein the non-oxidizing atmosphere is nitrogen.

10. The method according to claim 7, wherein cooking is carried out in a return flow.

11. The method according to claim 7, wherein the precipitate is produced by filtering.

12. The method according to claim 11, comprising washing the filter residue, drying the filter residue and grinding the filter residue.

13. The method according to claim 12, comprising washing the filter residue with hexane.

14. The method according to claim 12, comprising grinding the filter residue to a particle size of below 50 $\mu$m.

15. The method according to claim 7, comprising using an oil containing small quantities of fatty acids with straight-chain molecules or essentially straight-chain molecules.

* * * * *